United States Patent [19]

Mankovitz

[11] Patent Number: 5,385,733
[45] Date of Patent: * Jan. 31, 1995

[54] TOPICAL PREPARATION AND METHOD FOR SUPPRESSION OF SKIN ERUPTIONS CAUSED BY HERPES SIMPLEX VIRUS

[76] Inventor: Roy J. Mankovitz, 18057 Medley Dr., Encino, Calif. 91316

[*] Notice: The portion of the term of this patent subsequent to Jun. 1, 2010 has been disclaimed.

[21] Appl. No.: 104,193

[22] Filed: Aug. 9, 1993

Related U.S. Application Data

[63] Continuation-in-part of Ser. No. 884,659, May 15, 1992, abandoned, which is a continuation-in-part of Ser. No. 755,880, Sep. 6, 1991, Pat. No. 5,215,748, which is a continuation-in-part of Ser. No. 601,276, Oct. 22, 1990, abandoned.

[51] Int. Cl.$^6$ ............... A61K 35/78; A61K 31/05
[52] U.S. Cl. ........................ 424/195.1; 514/731
[58] Field of Search ............... 424/195.1; 514/731

[56] References Cited

U.S. PATENT DOCUMENTS

| | | | |
|---|---|---|---|
| 4,262,007 | 4/1981 | Sherrill | 514/421 |
| 4,350,787 | 9/1982 | Keith et al. | 424/346 |
| 4,382,886 | 5/1983 | Sosnowski | 260/107 |
| 5,215,748 | 6/1993 | Mankovitz | 424/195.1 |

OTHER PUBLICATIONS

J. Richards, et al., "Topical butylated hydroxytoluene treatment of genital herpes simplex virus infections of guinea pigs", Antiviral Res. 5, 281, 1985.
Lewis, Medical Botany, Wiley & Sons, London, p. 366, 1977.

*Primary Examiner*—Ronald W. Griffin
*Assistant Examiner*—Howard Lee
*Attorney, Agent, or Firm*—Roy J. Mankovitz

[57] ABSTRACT

A preparation and method for suppressing skin eruptions caused by herpes simplex virus in a human subject, comprising butylated hydroxytoluene in solution with oleum melaleucae alternifolia.

3 Claims, No Drawings

TOPICAL PREPARATION AND METHOD FOR SUPPRESSION OF SKIN ERUPTIONS CAUSED BY HERPES SIMPLEX VIRUS

CROSS REFERENCE TO PRIOR APPLICATIONS

This application is a continuation-in-part of my co-pending patent application Ser. No. 07/884,659, filed May 15, 1992, now abandoned, which is a continuation-in-part of my patent application Ser. No. 07/755,880, filed Sep. 6, 1991, and issued as U.S. Pat. No. 5,215,748, which is a continuation-in-part of my patent application Ser. No. 07/601,276, filed Oct. 22, 1990, now abandoned.

BACKGROUND OF THE INVENTION

This invention relates to topical antiviral preparations and, more particularly, to a topical preparation and method for suppression of skin eruptions caused by herpes simplex virus.

Several topical preparations have been developed in an attempt to control the severity and duration of vesicle eruption episodes in patients infected with herpes simplex type 1 (HSV-1) and type 2 (HSV-2). One such topical preparation is acyclovir ointment. A second preparation is disclosed in U.S. Pat. No. 4,350,707, issued Sep. 21, 1982, to Keith, et al. This preparation uses butylated hydroxytoluene (BHT) in an inert carrier such as mineral oil.

Both of these prior art topical preparations have proved to be only marginally effective in reducing the episode duration. Typically, use of these preparations reputedly reduces episode durations from seven days to three days. J. T. Richards, M. E. Katz, and E. R. Kern, in their report "Topical butylated hydroxytoluene treatment of genital herpes simplex virus infections of guinea pigs", Antiviral Research, 5 (1985) pp. 281–290, concluded that topical treatment of recurrent HSV-2 infections with BHT in mineral oil failed to alter the number of recurrent episodes or days with lesions.

SUMMARY OF THE INVENTION

It has been found that the topical application of the combination of butylated hydroxytoluene in solution with oleum Melaleucae alternifolia is effective in suppressing herpes simplex vesicle eruptions when used prophylactically, and is effective in treating existing eruptions to reduce their duration.

DESCRIPTION OF THE PREFERRED EMBODIMENTS

It has been found by the inventor that the topical application of oleum Melaleucae alternifolia is as effective as prior art preparations in reducing the duration of herpes simplex episodes, as measured from first eruption of a vesicle until complete clearing. Oleum Melaleucae alternifolia is a naturally occurring essential oil distilled from leaves of Melaleucae alternifolia, and is commonly referred to as tea tree oil. The oil consists chiefly of terpinenes, cymones, pinenes, terpineols, cineol, sesquinterpenes, and sequiterpene alcohols.

Tea tree oil, which is produced mostly in Australia, is well known for its antibacterial, antiseptic and antifungal properties. The oil has a very low toxicity, and is generally non-irritating even to sensitive tissues. A wide range of products are available which include tea tree oil as an active ingredient, including soaps, shampoos, creams, lotions, mouthwash, toothpaste and deodorants. There are indications in the literature that tree tea oil has been used to reduce the time of healing of cold sores. The tea tree oil used in the following tests was distilled and distributed by Thursday Plantation, New South Wales, Australia.

The following is a list of identifiable compounds found in samples of pure distilled oleum Melaleucae alternifolia as determined by a combination of analytical techniques including gas chromatography, and mass spectrometry.

| COMPOUND | % BY WEIGHT |
| --- | --- |
| 1. $\alpha$-Pinene | 2.8 |
| 2. Camphene | Tr |
| 3. $\beta$-Pinene | 0.59 |
| 4. Sabinene | 0.12 |
| 5. Myrcene | 0.52 |
| 6. $\alpha$-Phellandrene | 0.11 |
| 7. 1,4-Cineole | Tr |
| 8. $\alpha$-Terpinene | 2.74 |
| 9. Limonene | 3.09 |
| 10. 1,8-Cineole | 6.48 |
| 11. $\gamma$-Terpinene | 11.54 |
| 12. $p$-Cymeme | 11.42 |
| 13. Terpinolene | 2.36 |
| 14. Hexanol | Tr |
| 15. Allyl hexanoate | Tr |
| 16. $p,\alpha$-Dimethylstyrene | 0.07 |
| 17. a Sesquiterpene | 0.06 |
| 18. $\alpha$-Cubebene | 0.04 |
| 19. $\alpha$-Copaene | 0.10 |
| 20. Camphor | Tr |
| 21. $\alpha$-Gurjunene | 0.23 |
| 22. Linalool | 0.10 |
| 23. 1-Terpineol | Tr |
| 24. 1-Terpinen-4-ol | 38.52 |
| 25. $\beta$-Elemene | Tr |
| 26. Caryophyllene | Tr |
| 27. Aromadendrene | 2.35 |
| 28. $\beta$-Terpineol | 0.24 |
| 29. Alloaromadendrene | 0.45 |
| 30. Humulene | Tr |
| 31. $\gamma$-Muurolene | Tr |
| 32. $\alpha$-Terpineol | 3.61 |
| 33. Viridiflorene | 2.03 |
| 34. Piperitone | 0.08 |
| 35. $\alpha$-Muurolene | 0.12 |
| 36. Piperitol | 0.07 |
| 37. $\alpha$-Cadinene | 1.43 |
| 38. 4,10-Dimethyl-7-isopropyl bicyclo [4,4,0]-1,4-decadiene | 0.10 |
| 39. Nerol | Tr |
| 40. 8-$p$-Cymenol | 0.13 |
| 41. Calamenene | 0.10 |

It is generally believed that the 1,8-Cineole content assists the oil in penetration of tissue, but also produces tissue irritation in concentrations above 10%. Accordingly, it is preferable to maintain the 1,8-Cineole concentration below 7%. It is also generally believed that the terpinen-4-ol content assists in the healing of damaged tissue, and concentrations of 35% or more of this compound are desirable.

Three subjects having recurring herpes outbreaks (both Type 1 and Type 2) were tested using substantially pure undiluted tea tree oil in the following manner. Starting with the appearance of vesicles, the subjects applied a small amount of the oil directly to the infected area four times daily. In all subjects, the duration from first eruptions to clearing averaged three days. The average previous untreated episode for these subjects lasted seven days. The tests were repeated with the tea tree oil being applied only once per day starting with appearance of the vesicles, and the average duration was again reduced to three days.

The tea tree oil was then used prophylactically, whereby the oil was applied once daily to the general area in which vesicles had previously appeared, with the tests beginning at a time when the subjects were not experiencing an outbreak. Outbreaks still occurred at approximately the same intervals as when untreated, but the duration was again reduced to three days.

All of the above tests were repeated with a preparation of pure tea tree oil in solution with SD alcohol 40, where the tea tree oil concentration was 15% by weight of the preparation. The results in each test were substantially the same as with pure tea tree oil used alone.

The three subjects repeated all of the above tests using a preparation of undiluted tea tree oil in which was dissolved BHT in an amount of 5% by weight of the preparation. When the preparation was applied once at the first signs of vesicle eruption, the vesicles resolved in one day and did not advance to the crusting stage. When the preparation was used prophylactically once daily, no vesicle eruptions were noted by any subject, even though the usual herpes prodrome indications presented.

The subjects repeated the prophylactic test using a preparation comprising tea tree oil (15% by weight of the preparation), BHT (5% by weight of the preparation), the balance being SD alcohol 40 as a non-toxic diluent. As in the case of the use of undiluted tea tree oil in combination with BHT, the vesicle eruptions were completely suppressed.

Two of the subjects repeated the prophylactic test using a preparation comprising tea tree oil (15% by weight of the preparation), BHT (0.5% by weight of the preparation), the balance being SD alcohol 40 as a non-toxic diluent. The vesicle eruptions were again completely suppressed.

Two of the subjects repeated the prophylactic test using a preparation comprising tea tree oil (15% by weight of the preparation), BHT (0.05% by weight of the preparation), the balance being SD alcohol 40 as a non-toxic diluent. In one subject, the vesicle eruptions were completely suppressed. In the second subject, eruptions appeared, but the vesicles resolved in one day and did not advance to the crusting stage.

Two of the subjects repeated the prophylactic test using a preparation comprising tea tree oil (10% by weight of the preparation), BHT (0.05% by weight of the preparation), the balance being SD alcohol 40 as a non-toxic diluent. The vesicle eruptions were completely suppressed.

Two of the subjects repeated the prophylactic test using a preparation comprising tea tree oil (1% by weight of the preparation), BHT (0.05% by weight of the preparation), the balance being SD alcohol 40 as a non-toxic diluent. In the first subject, eruptions appeared, but the vesicles resolved in one day and did not advance to the crusting stage.

Two of the subjects repeated the prophylactic test using a preparation comprising tea tree oil (0.5% by weight of the preparation), BHT (0.05% by weight of the preparation), the balance being SD alcohol 40 as a non-toxic diluent. In both subjects, eruptions appeared, but the vesicles resolved in one day and did not advance to the crusting stage.

The above prophylactic test was repeated, again using the preparation comprising tea tree oil (0.5% by weight of the preparation), BHT (0.05% by weight of the preparation), the balance being SD alcohol 40 as a non-toxic diluent. In one subject, the vesicle eruptions were completely suppressed. In the second subject, eruptions appeared, but the vesicles resolved in one day and did not advance to the crusting stage.

While it is not known why the combination of tea tree oil and BHT produces such synergistic and unexpected results, it was noted that the BHT readily dissolves in tea tree oil in concentrations up to a saturation level of about 30%, and the tea tree oil provides rapid and deep penetration of the solution, without irritation of mucocutaneous areas. From the results of the tests described above, it appears that the preparation of the present invention exhibits synergistic effects for combinations of tea tree oil and BHT where the BHT concentration is as low as 0.05% by weight of the combination, and the tea tree oil concentration is as low as 0.5% by weight of the combination.

Recently, it has been discovered that the compound taxol, which is derived from the bark of Pacific yew trees, has the property of reducing the size of cancerous tumors, including breast, ovarian and lung tumors, in humans. Unfortunately, the harvesting of the yew bark destroys the trees, which have a 100 year growth cycle. Accordingly, attempts are being made to find alternate sources of this compound. One attempt currently under investigation involves the use of pinene, the main ingredient in turpentine.

In addition to its use as described above in a topical preparation for suppression of skin eruptions caused by herpes simplex virus, the inventor believes that the application of oleum Melaleucae alternifolia to cancerous tumors acts to reduce the size of those tumors in a manner similar to the action of taxol. While it is not known which of the compounds found in the oil provide the tumor reducing action, it is suspected that the terpinenes and terpineols play a major role.

While it is anticipated that direct injection into the tumor of the oil in combination with a suitable diluent will yield the best results, it may also be found that the oil is also effective in this application when administered orally or intravenously.

While the invention has been described, and preferred embodiments disclosed, it is anticipated that other modifications and adaptations will occur to those skilled in the art. It is intended, therefore, that the invention be limited only by the claims appended hereto.

What is claimed is:

1. A topical preparation for preventing and treating herpes simplex virus eruptions in human subjects comprising at least 0.05% by weight butylated hydroxytoluene and at least 0.5% by weight oleum melaleucae alternifolia.

2. A method for treating herpes simplex virus eruptions in a human subject, comprising topically administering at least 0.05% by weight butylated hydroxytoluene and at least 0.5% by weight oleum melaleucae alternifolia to the area of the eruptions.

3. A method for preventing skin eruptions due to herpes simplex virus eruptions in a human subject susceptible to said eruptions, comprising topically administering a preparation comprising at least 0.05% by weight butylated hydroxytoluene and at least 0.5% by weight oleum melaleucae alternifolia to an area where such eruptions are to occur.

* * * * *